United States Patent [19]

Sasaki et al.

[11] Patent Number: 5,072,061
[45] Date of Patent: Dec. 10, 1991

[54] 1,14-BIS(4-NITROPHENYL)-1,3,5,7,9,11,13-TETRADECAHEPTAENE AND PREPARATION METHOD THEREOF

[75] Inventors: Masaomi Sasaki, Susono; Tomoyuki Shimada; Mitsuru Hashimoto, both of Numazu, all of Japan

[73] Assignee: Ricoh Company, Ltd., Tokyo, Japan

[21] Appl. No.: 532,745

[22] Filed: Jun. 4, 1990

[30] Foreign Application Priority Data

Jun. 12, 1989 [JP] Japan ................... 1-149923

[51] Int. Cl.$^5$ .................. C07C 15/52; C07C 205/06; G03G 5/06
[52] U.S. Cl. .................... 568/931; 568/932; 568/939; 430/58
[58] Field of Search .............. 568/931, 939, 932; 430/58

[56] References Cited

U.S. PATENT DOCUMENTS

| 2,335,384 | 11/1943 | Bousquet et al. | 568/931 |
| 3,006,972 | 10/1961 | Fields et al. | 568/931 |
| 4,247,724 | 1/1981 | Gilbert | 568/931 |
| 4,335,055 | 6/1982 | Blaser et al. | 568/931 |
| 4,734,532 | 3/1988 | Kopp et al. | 568/931 |
| 4,780,559 | 10/1988 | Brown et al. | 568/933 |

FOREIGN PATENT DOCUMENTS 237544  5/1987  Japan .
232854A 8/1987  Japan .

Primary Examiner—Robert L. Stoll
Assistant Examiner—Chhaya Sayala
Attorney, Agent, or Firm—Oblon, Spivak, McClelland, Maier & Neustadt

[57] ABSTRACT 1,14-bis(4-nitrophenyl)-1,3,5,7,9,11,13-tetradecaheptaene having the following formula (I):

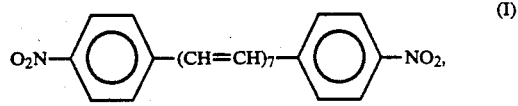

and a method of preparing the above-mentioned 1,14-bis(4-nitrophenyl)-1,3,5,7,9,11,13-tetradecaheptaene having formula (I) by allowing a phosphonium salt having formula (II) to react with 5-(4-nitrophenyl)-2,4-pentadiene-1-al having formula (III) in the presence of a basic catalyst:

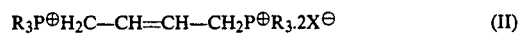

wherein R represents a phenyl group or an alkyl group having 1 to 6 carbon atoms; and X represents a halogen,

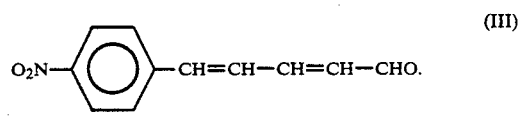

2 Claims, 1 Drawing Sheet FREQUENCY (cm$^{-1}$)

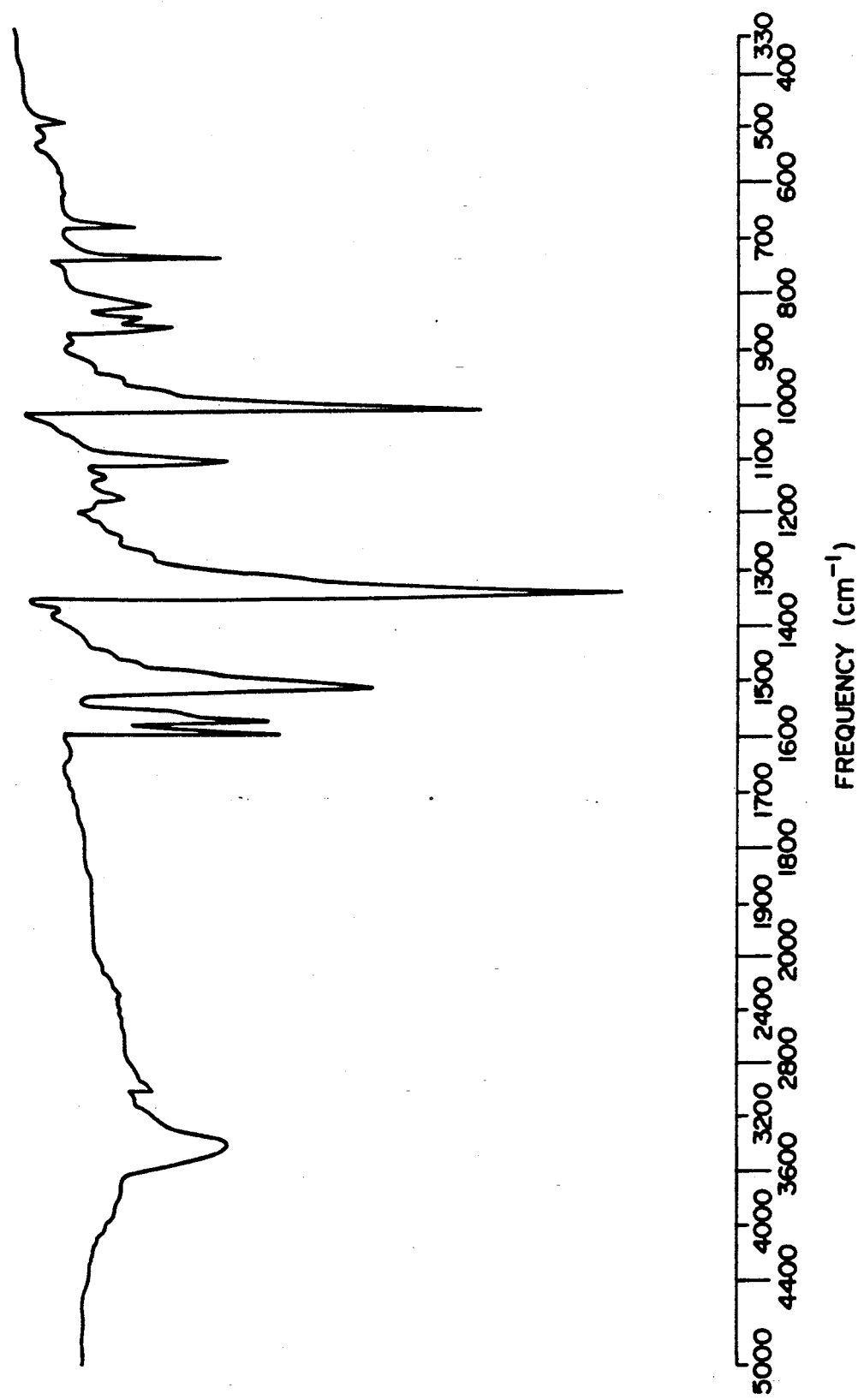

1,14-BIS(4-NITROPHENYL)-1,3,5,7,9,11,13-TETRADECAHEPTAENE AND PREPARATION METHOD THEREOF

BACKGROUND OF THE INVENTION

1. Field of the Invention

The present invention relates to 1,14-bis(4-nitrophenyl)-1,3,5,7,9,11,13-tetradecaheptaene and a method of preparing the same, which serves as a starting or intermediate material for preparing a bisazo compound which is effective as an organic photoconductive material for use in electrophotography.

2. Discussion of Background

It is conventionally known that particular azo compounds effectively serve as organic photoconductive materials for use in electrophotography, especially as charge generating materials for use in a two-layered type electrophotographic photoconductor. The two-layered type electrophotographic photoconductor is constructed in such a manner that (i) a charge generation layer comprising a charge generating material capable of generating charge carriers when exposed to light and (ii) a charge transport layer comprising a charge transporting material capable of performing efficient injection and transportation of the above-mentioned charge carriers are successively overlaid on an electroconductive support.

The azo compounds, which are conventionally used as the charge generating materials in the electrophotographic photoconductor, are, for example, benzidine type bisazo compounds as disclosed in Japanese Laid-Open Patent Applications 47-37543 and 52-55643 stilbene type bisazo compounds in Japanese Laid-Open Patent Application 52-8832; diphenylhexatriene type bisazo compounds in Japanese Laid-Open Patent Application 58-222152; and diphenylbutadiene type bisazo compounds in Japanese Laid-Open Patent Application 58-222153.

The photosensitivities of the two-layered type electrophotographic photoconductors using the above azo compounds as charge generating materials, however, are usually not high, so that such photoconductors are not always suitable for use in a high-speed copying apparatus.

In accordance with the recent development of laser printers, a demand for a photoconductor having high photosensitivity in the wavelength range of semiconductor laser is increasing. The above conventional two-layered electrophotographic photoconductors, however, do not necessarily satisfy all the requirements for the photoconductor for use in laser printers.

SUMMARY OF THE INVENTION

Accordingly, a first object of the present invention is to provide a starting or intermediate material for preparing a bisazo compound which is effective as an organic photoconductive material for use in an electrophotographic photoconductor, in particular, in a two-layered type electrophotographic photoconductor, capable of showing practically high photosensitivity when used not only in a high-speed copying apparatus, but also in a laser printer.

A second object of the present invention is to provide a method of preparing the above-mentioned starting or intermediate material.

The above-mentioned first object of the present invention can be achieved by 1,14-bis(4-nitrophenyl)-1,3,5,7,9,11,13-tetradecaheptaene having formula (I):

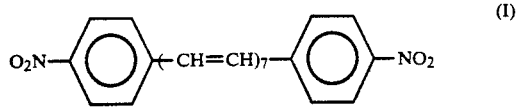

The above-mentioned second object of the present invention can be achieved by a preparation method comprising the step of allowing a phosphonium salt having formula (II) to react with 5-(4-nitrophenyl)-2,4-pentadiene-1-al having formula (III) in the presence of a basic catalyst:

wherein R represents a phenyl group or an alkyl group having to 6 carbon atoms; and X represents a halogen.

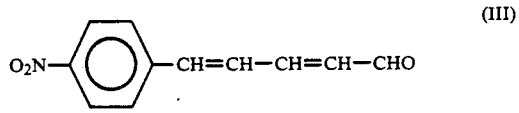

BRIEF DESCRIPTION OF THE DRAWING

In the drawing, the single FIGURE is an infrared absorption spectrum of 1,14-bis-(4-nitrophenyl)-1,3,5,7,9,11,13-tetradecaheptaene according to the present invention.

DESCRIPTION OF THE PREFERRED EMBODIMFNTS

An organic photoconductive material for use in an electrophotographic photoconductor can be prepared by the steps of (i) reducing 1,14-bis(4-nitrophenyl)-1,3,5,7,9,11, 13-tetradecaheptaene according to the present invention to obtain 1,14-bis(4-aminophenyl)-1,3,5,7,9,11,13-tetradecaheptaene, (ii) subjecting the thus obtained 1,14-bis(4-aminophenyl)-1,3,5,7,9,11,13-tetradecaheptaene to diazotization to obtain a tetrazonium salt compound having formula (IV), and (iii) subjecting the tetrazonium salt compound to a coupling reaction with a coupler to obtain a bisazo compound having formula (V) in the following reaction scheme:

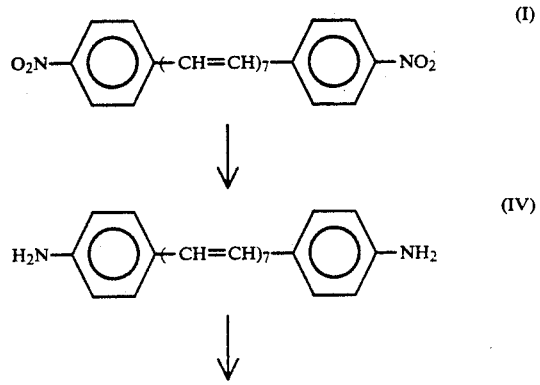

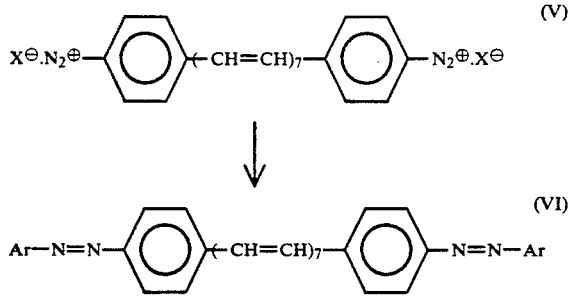

(V)

(VI)

In the above formula (V), $X^{\ominus}$ represents an anionic group. Examples of the above anionic group represented by $X^{\ominus}$ in formula (IV) are $Cl^-$, $Br^-$, $I^-$, $BF_4^-$, $B(C_6H_5)_4^-$, $ClO_4^-$, $SO_4^{2-}$,

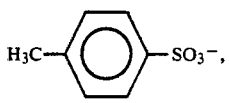

$AsF_6^-$ and $SbF_6^-$. Among them, $BF_4^-$ is preferable.

In the above formula (VI), Ar is a residual radical of a coupler represented by ArH, such as aromatic hydrocarbon compounds having a hydroxyl group and/or an amino group; heterocyclic compounds having a hydroxyl group and/or an amino group; and compounds having an aliphatic or aromatic enol-form ketone group, that is, an active ethylene group.

The present invention will now be explained in detail by referring to an example of a method of preparing 1,14-bis(4-nltrophenyl)-1,3,5,7,9,11,13-tetradecaheptaene.

As previously mentioned, 1,14-bis(4-nitrophenyl)-1,3,5,7,9,11,13-tetradecaheptaene having formula (I) can be prepared by allowing a phosphonium salt having formula (II) to react with 5-(4-nitrophenyl)-2,4-pentadiene-1-al having formula (III) in the presence of a basic catalyst:

$$R_3P^{\ominus}H_2C-CH=CH-CH_2P^{\oplus}R_2 \cdot 2X^{\ominus} \quad (II)$$

wherein R represents a phenyl group or an alkyl group having 1 to 6 carbon atoms; and X represents a halogen.

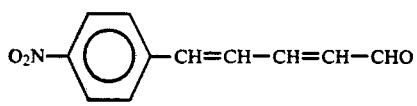

The above phosphonium salt of formula (II) can be easily prepared by allowing a halomethyl compound to react with the corresponding tri-phenylphosphine or tri-n-butylphosphine directly or in a solvent such as N,N-dimethylformamide, acetonitrile, chloroform, tetrahydrofuran, benzene, toluene, xylene, diethyl ether under application of heat.

The thus obtained phosphonium salt compound of formula (II) is then allowed to react with 5-(4-nitrophenyl)-2,4-pentadiene-1-al of formula (III) in the presence of a basic catalyst in the range of room temperature to about 100° C., whereby 1,14-bis(4-nitrophenyl)-1,3,5,7,9,11,13-tetradecaheptaene of formula (I) according to the present invention is prepared.

Specific examples of the basic catalyst used in the above reaction are sodium hydroxide, potassium hydroxide, sodium amide, sodium hydride, phenyllithium, n-butyl lithium, and alcoholate such as lithium methylate, sodium methylate and potassium-t-butoxide.

Examples of the solvent used in the above reaction are methanol, ethanol, isopropanol, butanol, 2-methoxyethanol, 1,2-dimethoxyethane, bis(2-methoxyethyl)ether, diethyl ether, dioxane, tetrahydrofuran, toluene, xylene, dimethyl sulfoxide, N,N-dimethylformamide, N-methylpyrrolidone and 1,3-dimethyl-2-imidazolidinone.

The reaction temperature may be set in a relatively wide range, depending upon the conditions such as (1) the stability of the employed solvent to the basic catalyst, (2) the reactivity of condensation components such as the phosphonium salt compound of formula (II) and 5-(4-nitrophenyl)-2,4-pentadiene-1-al of formula (III), and (3) the reactivity of the condensation components as a condensation agent in the presence of the basic catalyst.

For example, when a polar solvent is employed in the above reaction, it is preferable that the reaction temperature be in the range of room temperature to 100° C., more preferably in the range of room temperature to 80° C. The reaction temperature may be further elevated to shorten the reaction time or when a condensation agent having low activity is employed.

The thus obtained 1,14-bis(4-nitrophenyl)-1,3,5,7,9,11, 13-tetradecaheptaene according to the present invention can be used as it is, or after purification, it may be subjected to heat treatment together with a catalytic amount of iodine in an aromatic hydrocarbon type solvent such as toluene and xylene, as it remains crude or after purified. Thus, 1,14-bis(4-nitrophenyl)-1,3,5,7,9,11,13-tetradecaheptaene according to the present invention can be converted into an all trans form.

Other features of this invention will become apparent in the course of the following description of exemplary embodiment, which is given for illustration of the invention and is not intended to be limiting thereof.

EXAMPLE

[Preparation of 1,14-bis(4-nitrophenyl)-1,3,5,7,9,11,13-tetradecaheptaene]

A mixture of 7.40 g of 1,4-bis(triphenylphosphonium chloride)butene-2 and 4.63 g of 5-(4-nitrophenyl)-2,4-pentadiene-1-al was added to 300 ml of dried methanol. To the above mixture, 1.29 g of lithium methoxide was added over a period of 3 hours at 20° C. to 26° C. in a stream of nitrogen. After the completion of addition of the lithium methoxide, the mixture was stirred at room temperature for 5 hours. Crystals separated out in the reaction mixture. The crystals were filtered off, washed with water and methanol, and dried, so that 2.70 g of a crude product was obtained in the form of deep red powder.

The above obtained crude product was added to 300 ml together with a catalytic amount of iodine, followed by stirring at 75° C. in a stream of nitrogen for 27 hours. The reaction mixture was cooled to room temperature, and a precipltate was collected by filtration, whereby 2.47 g of deep red powder was obtained. The thus obtained powder was recrystallized from N,N-dimethylformamide, so that 1,14-bis[4-nitrophenyl)-1,3,5,7,9,11,13-tetradecaheptaene according to the present invention was obtained in the form of deep red needles.

The result of the thermal analysis of the thus obtained 1,14-bis(4-nitrophenyl)-1,3,5,7,9,11,13-tetradecaheptaene according to the present invention was as follows:

TG-DSC 259° C. (decomposed)

The results of the elemental analysis of the thus obtained product were as follows:

|  | % C | % H | % N |
|---|---|---|---|
| Calculated | 73.21 | 5.21 | 6.57 |
| Found | 72.97 | 5.07 | 6.51 |

FIGURE shows an infrared absorption spectrum of the above obtained 1,14-bis(4-nitrophenyl)-1,3,5,7,9,11,13-tetradecaheptaene according to the present invention, taken by use of a KBr tablet, which indicates absorption peaks at 1515 cm$^{-1}$ and 1340 cm$^{-1}$ characteristics of the nitro groups vibration and deformation vibration of the trans-olefin.

As previously mentioned, 1,14-bis(4-nitrophenyl)-1,3,5,7,9,11,13-tetradecaheptaene according to the present invention is a useful starting or intermedite material for preparation of a bisazo compound which serves as an organic photoconductive material used in an electrophotographic photoconductor, particularly in a two-layered type electrophotographic photoconductor. The above electrophotographic photoconductor shows high photosensitivity when used in a high-speed copying apparatus and a laser printer.

What is claimed is:

1. 1,14-bis(4-nitrophenyl)-1,3,5,7,9,11,13-tetradecaheptaene having formula (I):

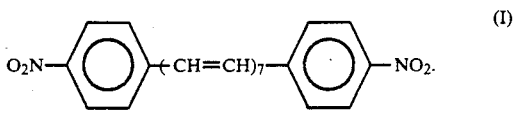

(I)

2. A method of preparing 1,14-bis(4-nitrophenyl)-1,3,5,7,9,11,13-tetradecaheptaene having formula (I):

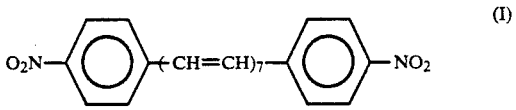

(I)

comprising the step of allowing a phosphonium salt having formula (II) to react with 5-(4-nitrophenyl)-2,4-pentadiene-1al having formula (III) in the presence of a basic catalyst:

(II)

wherein R represents a phenyl group or an alkyl group having 1 to 6 carbon atoms; and X represents a halogen,

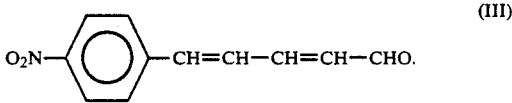

(III)

* * * * *

UNITED STATES PATENT AND TRADEMARK OFFICE
CERTIFICATE OF CORRECTION

PATENT NO. : 5,072,061

DATED : DECEMBER 10, 1991   Page 1 of 2

INVENTOR(S) : Masaomi SASAKI et al

It is certified that error appears in the above-identified patent and that said Letters Patent is hereby corrected as shown below:

Column 2, line 19, "$R_3P^{\oplus}H_2C-CH=CH-CH_2P^{\oplus}R_3 \sim 2X^{\ominus}$" should read -- $R_3P^{\oplus}H_2C-CH=CH-CH_2P^{\oplus}R_3 \cdot 2X^{\ominus}$ --.

Column 3, line 17, "$Cl^-$, $Br^-$, $I^-$, $BF_4^-$," should read -- $Cl^-$, $Br^-$, $I^-$, $BF_4^-$, $PF_6^-$, --;

line 35, "1,14-bis(4-nltrophenyl)-" should read -- 1,14-bis(4-nitrophenyl)- --;

line 44, "$R_3P^{\oplus}H_2C-CH=CH-CH_2P^{\oplus}R_2 \sim 2X^{\ominus}$" should read -- $R_3P^{\oplus}H_2C-CH=CH-CH_2P^{\oplus}R_3 \cdot 2X^{\ominus}$ --;

line 57, "tri-phenylphosphine" should read -- triphenylphosphine --.

Column 5, line 21, "nitro groups vibration" should read -- nitro groups and at 1005 $cm^{-1}$ characteristics of the out-of-plane vibration --.

UNITED STATES PATENT AND TRADEMARK OFFICE
CERTIFICATE OF CORRECTION

PATENT NO. : 5,072,061
DATED : DECEMBER 10, 1991
INVENTOR(S) : Masaomi SASAKI et al It is certified that error appears in the above-identified patent and that said Letters Patent is hereby corrected as shown below:

Column 6, line 20, "pentadiene-1al" should read -- pentadiene-1-al --;

line 22, "$R_3P^\oplus H_2C-CH=CH-CH_2P^\oplus R_3 \sim 2X^\ominus$" should read -- $R_3P^\oplus H_2C-CH=CH-CH_2P^\oplus R_3 \cdot 2X^\ominus$ --.

Signed and Sealed this

Twenty-second Day of June, 1993

Attest:

MICHAEL K. KIRK

*Attesting Officer*  *Acting Commissioner of Patents and Trademarks*